US00PP31320P3

(12) United States Plant Patent
van Zoest

(10) Patent No.: US PP31,320 P3
(45) Date of Patent: Jan. 7, 2020

(54) ***CLEMATIS* PLANT NAMED 'ZO08159'**

(50) Latin Name: ***Clematis* hybrid**
Varietal Denomination: Zo08159

(71) Applicant: Jan van Zoest, Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 15/998,160

(22) Filed: Jul. 9, 2018

(65) Prior Publication Data

US 2019/0246540 P1 Aug. 8, 2019

(30) Foreign Application Priority Data

Feb. 8, 2018 (QZ) ..... PBR 20180433

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

*Primary Examiner* — Susan McCormick Ewoldt
(74) *Attorney, Agent, or Firm* — Penny J. Aguirre

(57) ABSTRACT

A new cultivar of hybrid *Clematis*, 'Zo08159', that is characterized by its free flowering habit as a nursery plant, its terminal and axillary flowers, and its spring flowers and summer flowers with light to medium violet blue tepals.

2 Drawing Sheets

Botanical classification: *Clematis* hybrid.
Variety denomination: 'Zo08159'.

BACKGROUND OF THE INVENTION

The present invention relates to a new and distinct cultivar of *Clematis* of hybrid origin and will be referred to hereafter by its cultivar name 'Zo08159'.

*Clematis* 'Zo08159' is a deciduous plant grown for use as a landscape plant.

*Clematis* 'Zo08159' was derived from an ongoing breeding program by the Inventor at his nursery in Boskoop, The Netherlands. The goal of the selection was to select a new cultivar of *Clematis* that was free flowering in spring and summer with terminal and axillary flowers. 'Zo08159' was selected in 2012 and arose from a controlled cross made in 2004 between unnamed and unpatented plants from his breeding program; the female parent designated as No. 19960253 and the male parent designated as No. 20020196.

Asexual propagation of the new cultivar was first accomplished by softwood stem cuttings under the direction of the Inventor in Boskoop, The Netherlands in 2009. Asexual propagation by softwood stem cutting has determined that the characteristics of the new cultivar are stable and are reproduced true to type in successive generations.

STATEMENT DESIGNATING A GRACE PERIOD UNDER 120 (b)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventors; including but not limited to a disclosure on a website by J. van Zoest B. V in August of 2017.

SUMMARY OF THE INVENTION

The following traits have been repeatedly observed and represent the characteristics of the new cultivar as grown outdoors and observed for four years in Boskoop, The Netherlands. These attributes in combination distinguish *Clematis* 'Zo08159' as a unique cultivar of *Clematis*.

1. 'Zo08159' exhibits a free flowering habit as a nursery plant.
2. 'Zo08159' exhibits terminal and axillary flowers.
3. 'Zo08159' exhibits flowers in both spring and summer.
4. 'Zo08159' exhibits spring flowers and summer flowers with light to medium violet blue tepals.

The female parent of 'Zo08159' differs from 'Zo08159' in having flowers with very dark violet blue tepals, in having tepals that are flat in aspect (lack curled margins) and in lacking axillary flowers in spring. The male parent of 'Zo08159' differs from 'Zo08159' in having flowers with white tepals and stamens with white filaments and pale yellow connectives. 'Zo08159' can be most closely compared to the *Clematis* cultivar 'William Kennett' (not patented). 'William Kennett' is similar to 'Zo08159' in having flowers with violet blue tepals. 'William Kennett' differs from 'Zo08159' in deriving from a parentage of *Clematis lanuginsa* x *Clematis patens*, in having stamen filaments with a pale violet base, and in having leaflets that are longer and wider.

BRIEF DESCRIPTION OF THE DRAWINGS

The accompanying colored photographs illustrate the overall appearance and distinct characteristics of the new *Clematis*. The photographs were taken of a two-year-old plant as grown outdoors in a 2-liter rose container in Boskoop, The Netherlands.

The photograph in FIG. 1 provides a view of 'Zo08159' in bloom in summer.

Figure 1:
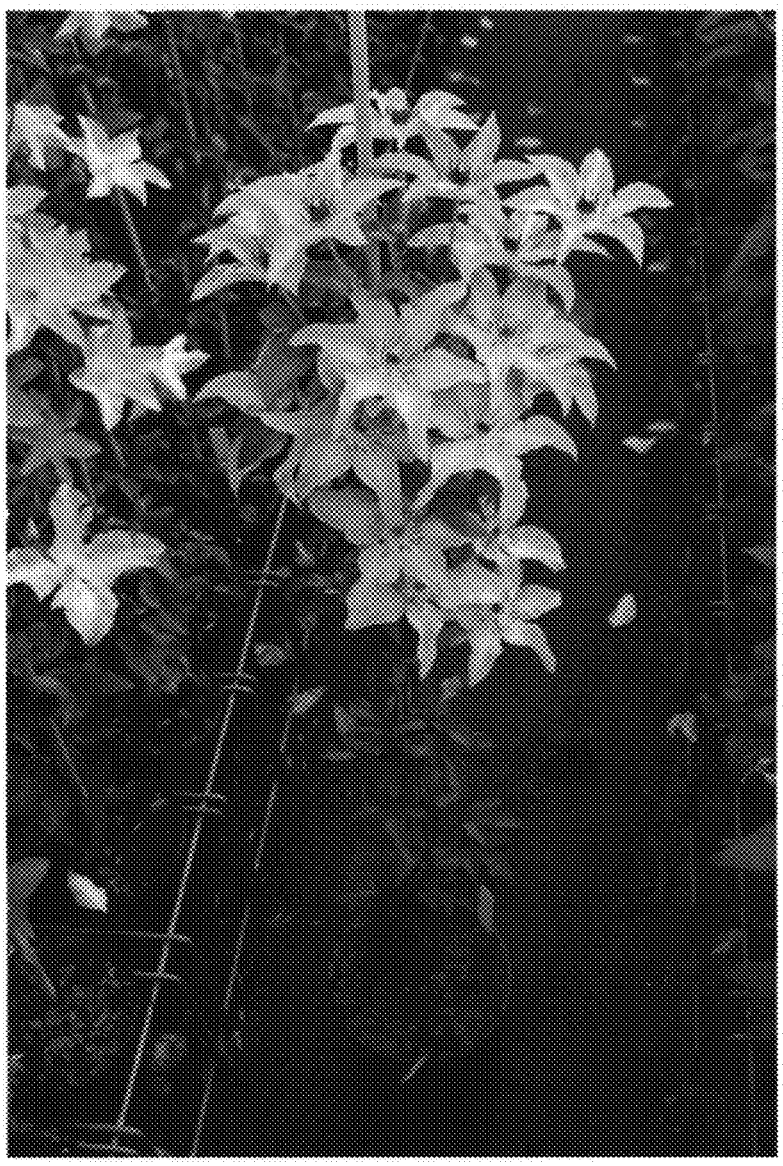
Figure 2:
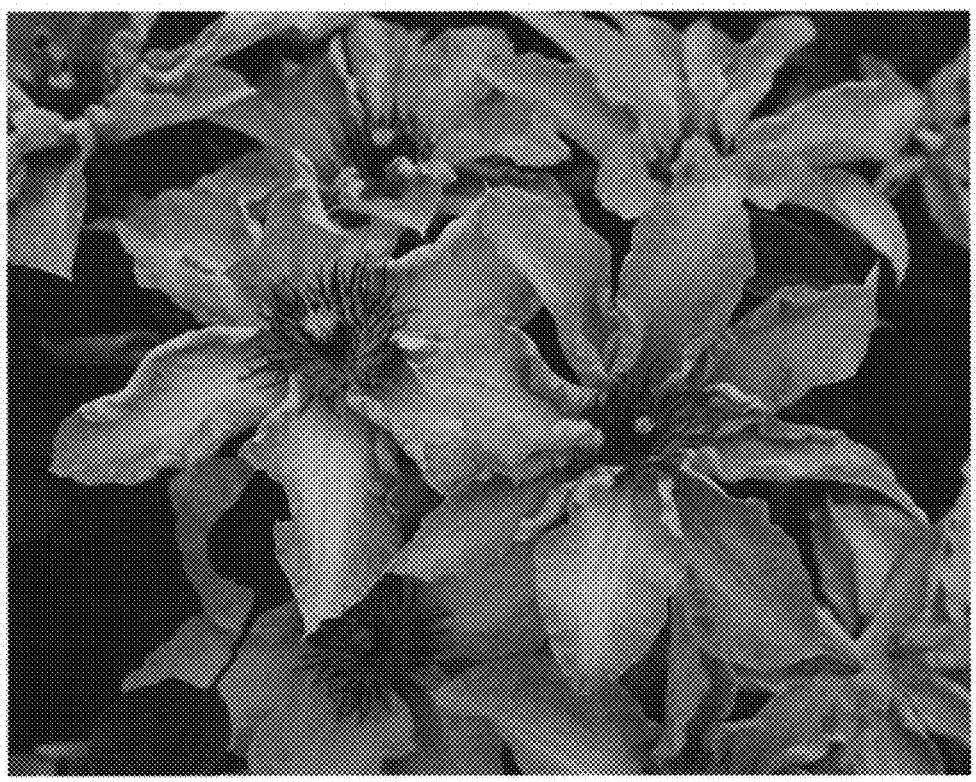

The photograph in FIG. 2 provides a view of the spring flowers of 'Zo08159'.

Figure 3:
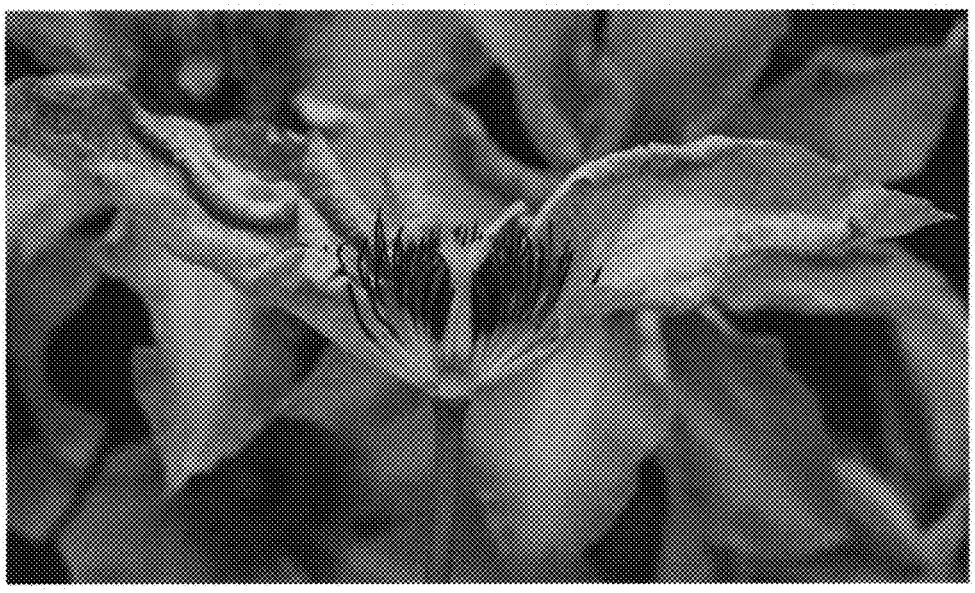

The photograph in FIG. 3 provides a close-up view of a cross section of a spring flower of 'Zo08159'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of two-year-old plants as grown outdoors in 2-Liter rose containers in Boskoop, The Netherlands. The phenotype of the new cultivar may vary with variations in environmental, climatic and cultural conditions, as the cultivar has not been tested under all possible environmental conditions. The color determination is in accordance with The 2001 Colour Chart of The Royal Horticultural Society, London, England, except where general color terms of ordinary dictionary significance are used.

General description:

*Botanical classification.*—*Clematis* 'Zo08159' (classified in the Patens Group).

*Blooming period.*—Spring from previous year's growth and summer from new growth.

*Plant type.*—Woody (stems overwinter).

*Plant habit.*—Climber.

*Height and spread.*—Three-year-old plant reaches an average of 2 m in height and 20 cm in spread at the base.

*Cold hardiness.*—At least to U.S.D.A. Zone 6.

*Culture.*—Moist but well-drained soils in full sun with the roots shaded.

*Diseases and pests.*—Susceptibility to powdery mildew caused by *Erysiphe polygoni* is unknown, no pest problems have been observed.

*Root description.*—Fleshy.

*Propagation.*—Softwood cuttings.

*Root initiation.*—Roots develop in 5 weeks in summer under greenhouse conditions.

*Time required for root development.*—75 to 90 days to fully develop in a 7-cm container from a 5-cm cutting.

*Growth rate.*—Moderately vigorous.

Stem description:

*Shape.*—Round with 6 angles.

*Stem color.*—N79B and becoming 166B with maturation.

*Stem size.*—Up to 2 m in length, an average of 3 mm in width.

*Stem surface.*—Sparsely hairy but more densely at the nodes.

*Internode length.*—7 to 12 cm.

*Branching.*—Primarily from the base.

Foliage description:

*Leaf arrangement.*—Opposite.

*Leaf division.*—Ternate.

*Leaf size.*—Up to 23 cm in length and 15 cm in width (including the petiole).

*Leaf attachment.*—Petiolate.

*Leaflet size.*—Up to 7 cm in length and 4 cm in width.

*Leaflet shape.*—Ovate.

*Leaflet base.*—Subcordate.

*Leaflet apex.*—Acuminate.

*Leaf fragrance.*—Honey-like fragrance when crushed.

*Leaf venation.*—Upper surface slightly reticulate and 138A in color, lower surface reticulate, glossy, and 143C in color.

*Leaflet margin.*—Entire with one wave.

*Leaf surface.*—Upper surface; glabrous with a few short hairs on the main veins, lower surface; glabrous but sparsely hairy with long hairs on main veins.

*Leaf color.*—Upper and lower surface; 147B.

*Petioles.*—Up to 10 cm in length, 1.5 mm in diameter, N79B in color, round in shape, surface sparsely hairy with long hairs, aspect sometimes curling.

*Petiolules.*—Terminal leaflet up to 7 cm in length, side leaflets up to 2 cm in length, 1 mm in width, round in shape, surface sparsely hairy with long hairs, N79B in color, strongly curly.

Inflorescence description:

*Inflorescence type.*—Solitary or a 3-flowered dichasial cyme.

*Inflorescence arrangement.*—Terminal and axillary on old wood in spring and young shoots in summer.

*Peduncles.*—Up to 11 cm in length, 3 mm in width, 144A in color, round in shape, surface very slightly 12-ribbed and sparsely hairy but more dense toward nodes.

*Pedicels.*—Up to 7 cm in length, 2.5 mm in diameter, 144A in color, round in shape, surface very slightly 12-ribbed and hairy with hairs denser near the flower.

*Flower buds.*—Upright, lanceolate in shape, up to 5 cm in length and 2.5 cm in diameter, N144D in color with seams 145D, surface hairy with villous seams.

*Flower fragrance.*—None.

*Lastingness of the flowers.*—Individual flowers last up to 10 days until the first tepal drops, followed by the stamens.

*Flower quantity.*—Up to 50 flowers on a 3-year-old plant.

*Flower type.*—Spreading.

*Flower aspect.*—Upright.

*Flower shape.*—Round.

*Flower size.*—8 to 16 cm in diameter and 2 cm in depth.

*Flower sex.*—Bisexual.

*Bracts.*—Simple, ovate in shape, up to 5 cm in length and 3 cm in width, acuminate apex, entire margin, color 143A on upper surface and 143B on lower surface, veins upper surface slightly reticulate and 138A in color, lower surface reticulate, glossy, and 143C in color, surface upper glabrous with main veins sparsely hairy.

*Tepal number.*—8 on spring flowers, 6 on summer flowers.

*Tepal shape.*—Broadly ovate.

*Tepal aspect.*—Curled inwards when opening, then fully spreading, overlapping.

*Tepal apex.*—Obtuse on spring flowers, acute-acuminate on summer flowers.

*Tepal base.*—Cuneate.

*Tepal margin.*—Slightly crinkled, curled inwards when flower opens, later fully spreading.

*Tepal surface*.—Upper surface; glabrous, main veins sparsely covered with short hairs, outer surface; villous, margins are glabrous and sparsely covered with short hairs.

*Tepal color*.—Upper surface; 94C with base 155D (slightly darker when opening and slightly lighter when fading), outer surface; 94D with 97D near middle, base 155D, apex 65B.

*Tepal size*.—Up to 8 cm in length and an average of 5 cm in width.

Reproductive organs:

*Gynoecium*.—Average of 50 to 60 pistils, up to 1.5 cm in length, ovary; 143C in color and silvery and hairy, style; 143C in color, hairy, stigma; straight in aspect, 69D in color, glabrous.

*Androecium*.—Filaments; 0.6 to 1.4 cm in length, 1 mm in width and linear in shape, surface is glabrous, 155D in color with upper ¼ 70D in color, anthers; 9 mm in length, 0.5 mm in width, linear in shape, and 59C in color, pollen; dull, 189D in color, moderate in quantity, connective; 0.5 mm in length, straight in aspect, apex obtuse, surface is glabrous and 59A in color.

*Seed*.—Seed head 4 cm in diameter and globular in shape, seed is 30 to 40 in quantity, an average of 4 mm in length and 165A in color.

It is claimed:

1. A new and distinct cultivar of *Clematis* plant named 'Zo08159' as herein illustrated and described.

* * * * *